(12) United States Patent
Ovalle et al.

(10) Patent No.: US 9,426,991 B2
(45) Date of Patent: Aug. 30, 2016

(54) SYNERGISTIC WEED CONTROL FROM APPLICATIONS OF AMINOCYCLOPYRACHLOR AND PICLORAM

(71) Applicant: Dow AgroSciences LLC, Indianapolis, IN (US)

(72) Inventors: Daniel Ovalle, Bogota D.C. (CO); Eduardo Posada, Bogota D.C. (CO)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 14/098,733

(22) Filed: Dec. 6, 2013

(65) Prior Publication Data

US 2014/0162878 A1 Jun. 12, 2014

Related U.S. Application Data

(60) Provisional application No. 61/736,127, filed on Dec. 12, 2012.

(51) Int. Cl.
*A01N 43/40* (2006.01)
*A01N 43/54* (2006.01)

(52) U.S. Cl.
CPC .................... *A01N 43/54* (2013.01)

(58) Field of Classification Search
USPC ................................ 504/130, 134
See application file for complete search history.

(56) References Cited

U.S. PATENT DOCUMENTS

| | | | |
|---|---|---|---|
| 3,940,260 A | 2/1976 | Kauffman | |
| 7,314,849 B2 | 1/2008 | Balko et al. | |
| 7,432,227 B2 | 10/2008 | Balko et al. | |
| 7,863,220 B2 | 1/2011 | Clark et al. | |
| 2009/0011936 A1 | 1/2009 | Hawkes et al. | |
| 2010/0016158 A1 | 1/2010 | Kilian et al. | |
| 2010/0048399 A1 | 2/2010 | Hacker et al. | |
| 2010/0069248 A1 | 3/2010 | Hacker et al. | |
| 2010/0205696 A1* | 8/2010 | Chen et al. | 800/300 |
| 2010/0279862 A1 | 11/2010 | Bickers et al. | |
| 2010/0285959 A1 | 11/2010 | Armel et al. | |
| 2011/0009264 A1 | 1/2011 | Hacker et al. | |
| 2011/0118120 A1 | 5/2011 | Corr et al. | |
| 2011/0190130 A1 | 8/2011 | Carranza Garzon | |
| 2011/0190134 A1 | 8/2011 | Jousseaume et al. | |
| 2011/0190136 A1 | 8/2011 | Hufnagl et al. | |
| 2011/0230349 A1 | 9/2011 | Buttimor | |
| 2011/0287932 A1 | 11/2011 | Hacker et al. | |
| 2011/0287935 A1 | 11/2011 | Patzoldt et al. | |
| 2011/0294663 A1 | 12/2011 | Hacker et al. | |
| 2012/0015808 A1 | 1/2012 | Rodriguez Contreras et al. | |
| 2012/0071320 A1 | 3/2012 | Atkinson et al. | |
| 2012/0115727 A1 | 5/2012 | Satchivi et al. | |
| 2012/0142532 A1 | 6/2012 | Wright et al. | |
| 2012/0149572 A1 | 6/2012 | Gewehr et al. | |
| 2012/0238449 A1 | 9/2012 | Mann | |
| 2013/0023413 A1 | 1/2013 | Hacker et al. | |
| 2014/0031214 A1 | 1/2014 | Yerkes et al. | |

FOREIGN PATENT DOCUMENTS

| | | |
|---|---|---|
| WO | 2009/103451 | 8/2009 |
| WO | 2010009819 | 1/2010 |
| WO | 2010/017921 | 2/2010 |
| WO | 2010/019377 | 2/2010 |
| WO | 2010/046422 | 4/2010 |
| WO | 2010059680 | 5/2010 |
| WO | 2010086437 | 8/2010 |
| WO | 2011019652 | 2/2011 |
| WO | 2012/037425 | 3/2012 |
| WO | 2013026811 | 2/2013 |

OTHER PUBLICATIONS

HCAPLUS abstract 1983:608033 (1983).*
EPA R.E.D. FACTS Picloram, EPA-738-F-95-018, Aug. 1995.*
Cabrera et al., "Sorption of the herbicide aminocyclopyrachlor by cation-modified clay minerals," European J. Soil Science, vol. 63, Issue 5 (Jul. 10, 2012), Abstract.
Lindenmayer, "Understanding Aminocyclopyrachlor Behavior in Soil and Plants," Dissertation, Colorado State University (Spring 2012).
Tomlin, C. D. S., Ed., The Pesticide Manual: A World Compendium, "Aminocyclopyrachlor," 15th ed., BCPC: Alton, 2009, pp. 33-34.
Tomlin, C. D. S., Ed., The Pesticide Manual: A World Compendium, "Picloram," 15th ed., BCPC: Alton, 2009, pp. 905-908.
Farm Chemical International, Crop Protection Database, "Aminocyclopyrachlor," available at http://www.farmchemicalsinternational.com/crop-protection-database/#/production/detail/1450606/ (accessed on Mar. 27, 2014).
Farm Chemical International, Crop Protection Database, "Picloram," available at http://www.farmchemicalsinternational.com/crop-protection-database/#/production/detail/308300/ (accessed on Mar. 27, 2014).
International Search Report issued on Mar. 18, 2014, in related International Patent Application No. PCT/US13/73841.
Picloram Product Safety Assessment, Dow Chemical Co., Sep. 12, 2009.

* cited by examiner

*Primary Examiner* — John Pak
(74) *Attorney, Agent, or Firm* — Michael R. Asam; Meunier Carling & Curfman, LLC

(57) ABSTRACT

Disclosed herein are herbicidal compositions comprising a synergistically herbicidal effective amount of (a) aminocyclopyrachlor, or an agriculturally acceptable salt or ester thereof, and (b) picloram, or an agriculturally acceptable salt or ester thereof. Also disclosed herein are methods of controlling undesirable vegetation, which comprise applying to vegetation or an area adjacent the vegetation or applying to soil or water to prevent the emergence or growth of vegetation (a) aminocyclopyrachlor, or an agriculturally acceptable salt or ester thereof, and (b) picloram, or an agriculturally acceptable salt or ester thereof, wherein (a) and (b) are each added in an amount sufficient to produce a synergistic herbicidal effect.

12 Claims, No Drawings

SYNERGISTIC WEED CONTROL FROM APPLICATIONS OF AMINOCYCLOPYRACHLOR AND PICLORAM

CROSS-REFERENCE TO RELATED APPLICATIONS

This application claims the benefit of priority to U.S. Provisional Patent Application No. 61/736,127 filed Dec. 12, 2012, the disclosure of which is incorporated herein by reference in its entirety.

FIELD OF THE DISCLOSURE

The present disclosure relates to herbicidal compositions comprising a synergistically herbicidal effective amount of (a) aminocyclopyrachloror an agriculturally acceptable salt or ester thereof, and (b) picloram or an agriculturally acceptable salt or ester thereof. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation.

SUMMARY OF THE DISCLOSURE

Herbicides of many types have been disclosed in the literature and a number are in commercial use. In some cases, herbicidal active ingredients have been found more effective in combination than when applied individually and this is referred to as "synergy" or "synergism." The present disclosure is based on the discovery that (a) aminocyclopyrachlor, or an agriculturally acceptable salt or ester thereof, and (b) picloram, or an agriculturally acceptable salt or ester thereof, display a synergistic herbicidal effect when applied in combination.

Accordingly, the present disclosure relates to herbicidal compositions comprising a synergistically herbicidal effective amount of (a) aminocyclopyrachlor, or an agriculturally acceptable salt or ester thereof, and (b) picloram, or an agriculturally acceptable salt or ester thereof. In some embodiments, (a) includes aminocyclopyrachlor in acid form. In some embodiments, (b) includes picloram potassium salt, picloram triisopropanolamine salt, picloram choline salt, or a combination thereof. The acid equivalent weight ratio of (a) to (b) can be from 1:300 to 2:1 (e.g., from 5:12 to 5:3). In some embodiments, the composition further comprises an additional pesticide (e.g., aminopyralid, amicarbazone, bromoxynil, chlorsulfuron, clopyralid, 2,4-D, dicamba, dichlorprop-P, diclosulam, diuron, florasulam, flucarbazone-sodium, flumetsulam, fluoroxypyr, glyphosate, glufosinate, imazamox, imazapyr, imazapic, imazaquin, imazethapyr, imazamethabenz, indaziflam, ioxynil, MCPA, mecoprop-P, metsulfuron-methyl, oxyfluorfen, penoxsulam, pinoxaden, pyroxsulam, rimsulfuron, sulfometuron, thifensulfuron-methyl, tebuthiuron, tribenuron-methyl, triclopyr, or agriculturally acceptable salts or esters or mixtures thereof). The additional pesticide can include 2,4-D choline salt, triclopyr choline salt, or a mixture thereof. In some embodiments, the composition is free of naptalam and salts or esters thereof. In some embodiments, the composition further comprises a herbicidal safener, an agriculturally acceptable adjuvant or carrier, or a combination thereof.

The present disclosure also relates to methods of controlling undesirable vegetation, which comprise applying to vegetation or an area adjacent the vegetation or applying to soil or water to prevent the emergence or growth of vegetation (a) aminocyclopyrachlor, or an agriculturally acceptable salt or ester thereof and (b) picloram, or an agriculturally acceptable salt or ester thereof, wherein (a) and (b) are each added in an amount sufficient to produce a synergistic herbicidal effect. In some embodiments, (a) and (b) are applied simultaneously. In some embodiments, (a) and (b) are applied postemergence to the undesirable vegetation. The undesirable vegetation can be controlled in, for instance, wheat, barley, corn or maize, sorghum, sugar cane, sugar beet, rice, cereals, conservation research program (CRP) lands, trees and vines, grasses grown for seed, oilseed rape or canola, pastures, grasslands, rangelands, industrial vegetation management (IVM), fallow land, rights-of-way, forestry, wildlife management areas, or turf. In some embodiments, the undesirable vegetation is a broadleaf weed. The undesirable vegetation can be controlled in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenylpyruvate dioxygenase (HPPD) inhibitors, protoporphyrinogen oxidase (PPO) inhibitors, triazines, bromoxynil, or combinations thereof. For example, the undesired vegetation can be controlled in phenoxy auxin tolerant crops and the phenoxy auxin tolerant crops have tolerance conferred by an AAD12 gene. In some embodiments, the undesirable vegetation is resistant to auxinic herbicides. In some embodiments, (a) is applied in an amount of from 8-240 grams of acid equivalent per hectare (g ae/ha). In some embodiments, (b) is applied in an amount of from 120-2400 g ae/ha.

The description below sets forth details of one or more embodiments of the present disclosure. Other features, objects, and advantages will be apparent from the description and from the claims.

DETAILED DESCRIPTION

The present disclosure relates to herbicidal compositions comprising a synergistically herbicidal effective amount of (a) aminocyclopyrachlor, or an agriculturally acceptable salt or ester thereof, and (b) picloram, or an agriculturally acceptable salt or ester thereof. The present disclosure also relates to methods for controlling undesirable vegetation.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Aminocyclopyrachlor

Compositions and methods of the present disclosure can include aminocyclopyrachloror an agriculturally acceptable salt or ester thereof. Aminocyclopyrachlor, shown below, is a herbicide that can be used to control broadleaf weeds in, for instance, lawns (e.g., residential, industrial, and institutional), golf courses, parks, cemeteries, athletic fields, sod farms, range and pasture, IVM, rights-of-way, roadsides, railroads, and other crop and non-crop uses. Its herbicidal activity is described in Tomlin, C. D. S., Ed. *The Pesticide Manual: A World Compendium*, 15$^{th}$ ed., BCPC: Alton, 2009 (hereinafter "*The Pesticide Manual, Fifteenth Edition, 2009*").

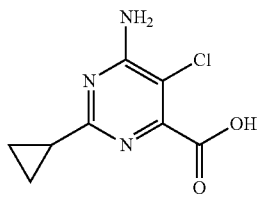 [SMILES: Nc1nc(C2CC2)nc(C(=O)O)c1Cl]

In some embodiments, the aminocyclopyrachlor is in acid form and is 6-amino-5-chloro-2-cyclopropylpyrimidine-4-carboxylic acid (6-amino-5-chloro-2-cyclopropyl-4-pyrimidinecarboxylic acid). In some embodiments, the aminocyclopyrachlor is in the form of an agriculturally acceptable salt or ester thereof. Exemplary agriculturally acceptable salts or esters of aminocyclopyrachlor include, but are not limited to, sodium salts, potassium salts, ammonium salts or substituted ammonium salts (e.g., mono-, di- and tri-$C_1$-$C_8$-alkylammonium salts such as methyl ammonium, dimethylammonium and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts), and their diglycolamine salts and their esters (e.g., its $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters, and aryl esters such as benzyl). Exemplary agriculturally acceptable salts of aminocyclopyrachlor can include aminocyclopyrachlor-sodium, aminocyclopyrachlor-potassium, aminocyclopyrachlor choline salt, or mixtures thereof. An exemplary agriculturally acceptable ester of aminocyclopyrachlor can include aminocyclopyrachlor-methyl. Aminocyclopyrachloror agriculturally acceptable salts or esters thereof are or have been commercially available, for example, from DuPont Crop Protection under the trademarks IMPRELIS®, STREAMLINE®, REJUVRAO, VIEWPOINT®, METHOD®, and PLAINVIEW®.

The aminocyclopyrachloror an agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the aminocyclopyrachloror agriculturally acceptable salt or ester thereof is applied to vegetation or an area adjacent the vegetation or applied to soil or water to prevent the emergence or growth of vegetation in an amount of 8 grams of acid equivalent per hectare (g ae/ha) or greater (e.g., 10 g ae/ha or greater, 15 g ae/ha or greater, 20 g ae/ha or greater, 25 g ae/ha or greater, 30 g ae/ha or greater, 35 g ae/ha or greater, 40 g ae/ha or greater, 45 g ae/ha or greater, 50 g ae/ha or greater, 55 g ae/ha or greater, 60 g ae/ha or greater, 65 g ae/ha or greater, or 70 g ae/ha or greater). In some embodiments, the aminocyclopyrachloror agriculturally acceptable salt or ester thereof is applied to vegetation or an area adjacent the vegetation or applied to soil or water to prevent the emergence or growth of vegetation in an amount of 240 g ae/ha or less (e.g., 230 g ae/ha or less, 220 g ae/ha or less, 210 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, 130 g ae/ha or less, 120 g ae/ha or less, 110 g ae/ha or less, 100 g ae/ha or less, 90 g ae/ha or less, 80 g ae/ha or less, 70 g ae/ha or less, 60 g ae/ha or less, 50 g ae/ha or less, 40 g ae/ha or less, 30 g ae/ha or less, 25 g ae/ha or less, 20 g ae/ha or less, or 15 g ae/ha or less). In some embodiments, the aminocyclopyrachloror agriculturally acceptable salt or ester thereof is applied to vegetation or an area adjacent the vegetation or applied to soil or water to prevent the emergence or growth of vegetation in an amount of from 8-240 g ae/ha (e.g., from 10-220 g ae/ha, from 12-200 g ae/ha, from 14-180 g ae/ha, from 16-160 g ae/ha, or from 18-150 g ae/ha).

Picloram

Compositions and methods of the present disclosure can include picloram or an agriculturally acceptable salt or ester thereof. Picloram (i.e., 4-amino-3,5,6-trichloro-2-pyridinecarboxylic acid), shown below, is a herbicide that can be used to control broadleaf weeds and woody plants in, for instance, cereal crops, rights-of-way, forest sites, pastures, fallow, turf, rangelands, forest, and industrial applications. Its herbicidal activity is described in The Pesticide Manual, Fifteenth Edition, 2009.

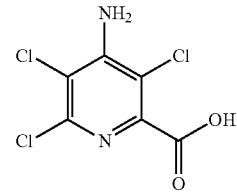 [SMILES: Nc1c(Cl)c(Cl)nc(C(=O)O)c1Cl]

Picloram can be provided in its acid form (as shown above), or as an agriculturally acceptable salt or ester thereof. Exemplary agriculturally acceptable salts or esters of picloram include, but are not limited to, sodium salts, potassium salts, ammonium salts or substituted ammonium salts, in particular mono-, di- and tri-$C_1$-$C_8$-alkylammonium salts such as methyl ammonium, dimethylammonium and isopropylammonium (e.g., triisopropanolammonium), mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl) ammonium salts, their diglycolamine salts and their esters, in particular its $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, 2-ethylhexyl and butoxyethyl esters. Exemplary agriculturally acceptable salts or esters of picloram can include picloram-potassium, picloram choline, picloram-tris(2-hydroxypropyl)ammonium, picloram-methyl, and mixtures thereof. In some embodiments, the picloram is provided as an amine salt, such as picloram-olamine, dimethylamine (DMA) salt, monoethanolamine (MEA) salt, isooctyl/ethylhexyl (JOE) salt, triisopropanolamine (TIPA) salt, or a mixture thereof. Picloram and agriculturally acceptable salts or esters thereof are or have been commercially available, for example, under the trademarks TRIUMPH® 22K and TRIUMPH® K (by ALBAUGH, INC.); OUTPOST®22K and TORDON® 22K (by DOW AGROSCIENCES LLC); PICLO® (by FERTIAGRO PTE. LTD.); GILCLORAM® (by GILMORE MARKETING & DEVELOPMENT, INC.); TROOPER® 22K (by NUFARM AMS. INC.); and SUN-CLORAN® (by SUNDAT (S) PTE. LTD.).

The picloram or an agriculturally acceptable salt or ester thereof described herein can be used in an amount sufficient to induce a herbicidal effect. In some embodiments, the picloram or agriculturally acceptable salt or ester thereof is applied to vegetation or an area adjacent the vegetation or applied to soil or water to prevent the emergence or growth of vegetation in an amount of 120 grams of acid equivalent per hectare (g ae/ha) or greater (e.g., 130 g ae/ha or greater, 140 g ae/ha or greater, 150 g ae/ha or greater, 160 g ae/ha or greater, 170 g ae/ha or greater, 180 g ae/ha or greater, 190 g ae/ha or greater, 200 g ae/ha or greater, 210 g ae/ha or greater, 220 g ae/ha or greater, 230 g ae/ha or greater, 240 g ae/ha or greater, 260 g ae/ha or greater, 280 g ae/ha or greater, 300 g ae/ha or greater, 350 g ae/ha or greater, 400 g ae/ha or greater, 450 g ae/ha or greater, 500 g ae/ha or greater, 600 g ae/ha or greater, 700 g ae/ha or greater, 800 g ae/ha or greater, 900 g ae/ha or greater, 1000 g ae/ha or greater, 1200 g ae/ha or greater, 1400 g ae/ha or greater, 1600 g ae/ha or greater, 1800 g ae/ha or greater, 2000 g ae/ha or greater, or 2200 g ae/ha or greater). In some embodiments, the picloram or agriculturally acceptable salt or ester thereof is applied to vegetation or an area adjacent the vegetation or applied to soil or water to prevent the emergence or growth of vegetation in an amount of 2400 g ae/ha or less (e.g., 2300 g ae/ha or less, 2100 g ae/ha or less, 1900 g ae/ha or less, 1700 g ae/ha or less, 1500 g ae/ha or less, 1300 g ae/ha or less, 1100 g ae/ha or less, 900 g ae/ha or less, 800 g ae/ha or less, 700 g ae/ha or less, 600 g ae/ha or less, 500 g ae/ha or less, 400 g ae/ha or less, 350 g ae/ha or less, 300 g ae/ha or less, 250 g ae/ha or less, 200 g ae/ha or less, 190 g ae/ha or less, 180 g ae/ha or less, 170 g ae/ha or less, 160 g ae/ha or less, 150 g ae/ha or less, 140 g ae/ha or less, or 130 g ae/ha or less). In some embodiments, the picloram or agriculturally acceptable salt or ester thereof is applied to vegetation or an area adjacent the vegetation or applied to soil or water to prevent the emergence or growth of vegetation in an amount of from 120-2400 g ae/ha (e.g., from 130-2000 g ae/ha, from 140-1500 g ae/ha, from 150-1000 g ae/ha, from 160-800 g ae/ha, from 170-600 g ae/ha, or from 180-500 g ae/ha).

Herbicidal Mixtures or Combinations

The (a) aminocyclopyrachloror an agriculturally acceptable salt or ester thereof is mixed with or applied in combination with (b) picloram or an agriculturally acceptable salt or ester thereof in an amount sufficient to induce a synergistic herbicidal effect. In some embodiments, (a) and (b) are used in an amount sufficient to induce a synergistic herbicidal effect while still showing good crop compatibility (i.e. their use in crops does not result in increased damage to crops when compared to the individual application of the herbicidal compounds (a) or (b)). As described in the *Herbicide Handbook* of the Weed Science Society of America, Ninth Edition, 2007, p. 429, "'synergism' [is] an interaction of two or more factors such that the effect when combined is greater than the predicted effect based on the response to each factor applied separately." Synergistic in the herbicide context can mean that the use of (a) and (b) as defined above results in an increased weed control effect compared to the weed control effects that are possible with the use of (a) or (b) alone. In some embodiments, the damage or injury to the undesired vegetation caused by the compositions and methods disclosed herein is evaluated using a scale from 0% to 100%, when compared with the untreated control vegetation, wherein 0% indicates no damage to the undesired vegetation and 100% indicates complete destruction of the undesired vegetation. In some embodiments, Colby's formula is applied to determine whether using (a) and (b) in combination shows a synergistic effect: S. R. Colby, *Calculating Synergistic and Antagonistic Responses of Herbicide Combinations*, WEEDS 15, p. 22 (1967)

$$E = X + Y - \frac{X * Y}{100}$$

wherein
X=effect in percent using (a) aminocyclopyrachloror an agriculturally acceptable salt or ester thereof at an application rate a;
Y=effect in percent using (b) picloram or an agriculturally acceptable salt or ester thereof at an application rate b;
E=expected effect in percent (%) of (a)+(b) at application rates a and b.

In Colby's equation, the value E corresponds to the effect (plant damage or injury) that is to be expected if the activity of the individual compounds is additive. If the observed effect is higher than the value E calculated according to the Colby equation, then a synergistic effect is present according to the Colby equation.

In some embodiments, the compositions and methods disclosed herein are synergistic as defined by the Colby equation. In some embodiments, the joint action of aminocyclopyrachloror an agriculturally acceptable salt or ester thereof and picloram or an agriculturally acceptable salt or ester thereof results in enhanced activity against undesired vegetation (via synergism), even at application rates below those typically used for the pesticide to have a herbicidal effect on its own. In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e. they effect damaging of undesired vegetation more quickly compared with application of the individual herbicides).

In some embodiments, the acid equivalent weight ratio of (a) aminocyclopyrachloror an agriculturally acceptable salt or ester thereof to (b) picloram or an agriculturally acceptable salt or ester thereof that is sufficient to induce a synergistic herbicidal effect is at least 1:300 (e.g., at least 1:275, at least 1:250, at least 1:225, at least 1:200, at least 1:175, at least 1:150, at least 1:125, at least 1:100, at least 1:75, at least 1:60, at least 1:45, at least 1:30, at least 1:15, at least 1:13, at least 1:11, at least 1:9, at least 1:7, at least 1:6, at least 1:5, at least 1:4, at least 1:3, at least 1:2, or at least 1:1). In some embodiments, the acid equivalent weight ratio of (a) to (b) that is sufficient to induce a synergistic herbicidal effect is 2:1 or less (e.g., 1:1 or less, 1:2 or less, 1:3 or less, 1:4 or less, 1:5 or less, 1:6 or less, 1:7 or less, 1:8 or less, 1:9 or less, 1:10 or less, 1:15 or less, 1:20 or less, 1:25 or less, 1:30 or less, 1:35 or less, 1:40 or less, 1:45 or less, 1:50 or less, 1:60 or less, 1:70 or less, 1:80 or less, 1:90 or less, 1:100 or less, 1:125 or less, 1:150 or less, 1:175 or less, 1:200 or less, 1:225 or less, 1:250 or less, or 1:275 or less). In some embodiments, the acid equivalent weight ratio of (a) to (b) is from 1:300 to 2:1 (e.g., from 1:150 to 2:1, from 1:75 to 2:1, from 1:40 to 1.9:1, from 1:20 to 1.8:1, from 1:10 to 1.7:1, from 1:5 to 5:3, from 1:3 to 5:3, or from 5:12 to 5:3).

Formulations

The present disclosure also relates to formulations of the compositions and methods disclosed herein. In some embodiments, the formulation can be in the form of a single package formulation including both (a) aminocyclopyrachloror an agriculturally acceptable salt or ester thereof and (b) picloram or an agriculturally acceptable salt or ester thereof. In some embodiments, the formulation can be in the form of a single package formulation including both (a) and (b) and further including at least one additive. In some embodiments, the formulation can be in the form of a two-package formulation, wherein one package contains (a) and optionally at least one additive while the other package contains (b) and optionally at least one additive. In some embodiments of the two-package formulation, the formulation including (a) and optionally at least one additive and the formulation including (b) and optionally at least one additive are mixed before application and then applied simultaneously. In some embodiments, the mixing is performed as a tank mix (i.e., the formulations are mixed immediately before or upon dilution with water). In some embodiments, the formulation including (a) and the formulation including (b) are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a) and (b) is present in suspended, emulsified, or dissolved form. Exemplary formulations include, but are not limited to, aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, and materials for spreading or granules.

In some embodiments, (a) aminocyclopyrachloror an agriculturally acceptable salt or ester thereof and/or (b) picloram or an agriculturally acceptable salt or ester thereof is an aqueous solution that can be diluted before use. In some embodiments, (a) and/or (b) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the aminocyclopyrachloror agriculturally acceptable salt or ester thereof. In some embodiments, the additive is premixed with the picloram or agriculturally acceptable salt or ester thereof. In some embodiments, the additive is premixed with the aminocyclopyrachloror agriculturally acceptable salt or ester and the picloram or agriculturally acceptable salt or ester thereof.

In some embodiments, the additive is an additional pesticide. Exemplary additional pesticides include, but are not limited to, 2,4-D, acetochlor, aclonifen, amicarbazone, 4-aminopicolinic acid based herbicides, such as halauxifen, halauxifen-methyl, and those described in U.S. Pat. No. 7,314,849 (B2) and U.S. Pat. No. 7,432,227 (B2), amidosulfuron, aminopyralid, aminotriazole, ammonium thiocyanate, asulam, atrazine, beflubutamid, benazolin, bentazone, bifenox, bromacil, bromoxynil, butachlor, butafenacil, butralin, butroxydim, carbetamide, carfentrazone, carfentrazone-ethyl, chlormequat, chlorsulfuron, chlortoluron, cinidon-ethyl, clethodim, clodinafop-propargyl, clomazone, clopyralid, cyanazine, cyclosulfamuron, cycloxydim, dicamba, dichlobenil, dichlorprop-P, diclofop-methyl, diclosulam, diflufenican, diflufenzopyr, dimefuron, dimethachlor, diquat, diuron, EPTC, ethoxysulfuron, fenoxaprop, fenoxaprop-ethyl, fenoxaprop-ethyl+isoxadifen-ethyl, fenoxaprop-P-ethyl, fenoxasulfone, flazasulfuron, florasulam, fluazifop, fluazifop-P-butyl, flucarbazone, flucarbazone-sodium, flucetosulfuron (LGC-42153), flufenacet, flumetsulam, flumioxazin, flupyrsulfuron, fluoroxypyr, fluoroxypyr-meptyl, flurtamone, glufosinate, glufosinate-ammonium, glyphosate, haloxyfop-methyl, haloxyfop-R, hexazinone, imazamethabenz, imazamox, imazapic, imazapyr, imazaquin, imazethapyr, imazosulfuron, indanofan, indaziflam, iodosulfuron, iodosulfuron-ethyl-sodium, ioxynil, isoproturon, isoxaben, isoxaflutole, lactofen, linuron, MCPA, MCPB, mecoprop-P, mesosulfuron, mesosulfuron-ethyl sodium, metazochlor, metosulam, metribuzin, metsulfuron, metsulfuron-methyl, MSMA, napropamide, norfurazon, orthosulfamuron, oryzalin, oxadiargyl, oxadiazon, oxyfluorfen, paraquat, pendimethalin, penoxsulam, picolinafen, pinoxaden, primisulfuron, profluazol, propaquizafop, propoxycarbazone, propyzamide, prosulfocarb, prosulfuron, pyraflufen-ethyl, pyrasulfotole, pyribenzoxim (LGC-40863), pyroxsulam, pyroxasulfone, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tepraloxidim, terbacil, terbutryn, thiazopyr, thifensulfuron, thifensulfuron-methyl, topramezone, tralkoxydim, triasulfuron, tribenuron, tribenuron-methyl, triafamone, triclopyr, and trifluralin, and agriculturally acceptable salts, esters and mixtures thereof. In some embodiments, the additional pesticide includes 2,4-D choline salt, triclopyr choline salt, aminopyralid choline salt, or a mixture thereof.

In some embodiments, the compositions and methods disclosed herein do not incorporate naptalam (i.e., N-1-naphthylphthalamic acid or NPA) or the salts or esters thereof. In some embodiments, the compositions and methods disclosed herein are free of naptalam or the salts or esters thereof. In some embodiments, naptalam or the salts or esters thereof are not applied to the vegetation, the area adjacent to the vegetation, the soil, or the water, in the methods disclosed herein.

In some embodiments, the aminocyclopyrachloror an agriculturally acceptable salt or ester thereof is provided in a premixed formulation with an additional pesticide. In some embodiments, the aminocyclopyrachloror an agriculturally acceptable salt or ester thereof is premixed with, chlorsulfuron, dicamba, imazapyr, glufosinate, glyphosate, MCPA, metsulfuron-methyl, sulfometuron, or mixtures thereof. Exemplary premixes of aminocyclopyrachloror an agriculturally acceptable salt or ester thereof and an additive that are or have been commercially available include, but are not limited to, PERSPECTIVE® (a premix incorporating chlorsulfuron by DuPont Crop Protection), VIEWPOINT®

(a premix incorporating imazapyr and metsulfuron-methyl by DuPont Crop Protection), PLAINVIEW® (a premix incorporating sulfometuron and chlorsulfuron by DuPont Crop Protection), or STREAMLINE® (a premix incorporating metsulfuron-methyl by DuPont Crop Protection).

In some embodiments, the picloram or an agriculturally acceptable salt or ester thereof is provided in a premixed formulation with an additional pesticide. In some embodiments, the picloram or an agriculturally acceptable salt or ester thereof is premixed with 2,4-D, dicamba, fluoroxypyr, metsulfuron-methyl, oxyfluorfen, triclopyr, or mixtures thereof. Exemplary premixes of picloram or an agriculturally acceptable salt or ester thereof and an additive that are or have been commercially available include, but are not limited to, ARENA® (a premix incorporating 2,4-D by Stockton Agrimor AG), CAMPERO® (a premix incorporating 2,4-D by Investa S.A.), EXTERMINATOR® (a premix incorporating 2,4-D by Dupocsa, Protectores Quimicos para el Campo S.A.), GRAZON P+D® (a premix incorporating 2,4-D by Dow AgroSciences LLC), GUNSLINGER IVM® (a premix incorporating 2,4-D by Albaugh, Inc.), GUNSLINGER® (a premix incorporating 2,4-D by Albaugh, Inc.), HIREDHAND® P+D (a premix incorporating 2,4-D by Dow AgroSciences, LLC), PATHWAY® (a premix incorporating 2,4-D by Dow AgroSciences LLC), POTRERON® (a premix incorporating 2,4-D by Insecticidas Internacionales C.A.), STOKE® (a premix incorporating 2,4-D by Dupocsa, protectores Quimicos para el Campo S.A.), TALION® (a premix incorporating 2,4-D by Stockton Agrimor AG), TERMINATOR® (a premix incorporating 2,4-D by Dupocsa, Protectores Quimicos para el Campo S.A.), TORDON® 101 (a premix incorporating 2,4-D by Dow AgroSciences LLC), TROOPER® P+D (a premix incorporating 2,4-D by Nufarm Ams. Inc.), TROTON® (a premix incorporating 2,4-D by Proficol), Turuna® (a premix incorporating 2,4-D by Stockton Agrimor AG), TROOPER® EXTRA (a premix incorporating 2,4-D and dicamba by Nufarm Ams. Inc.), SURMOUNT® (a premix incorporating fluoroxypyr by Dow AgroSciences LLC), TROOPER® PRO (a premix incorporating fluoroxypyr by Nufarm Ams. Inc.), KAPUT® (a premix incorporating metsulfuron-methyl by Insecticidas Internacionales C.A.), SOCIO® (a premix incorporating metsulfuron-methyl by Invesa S.A.), PYCUS ENCAPS® (a premix incorporating oxyfluorfen by Zelam Ltd.), and VICTORY GOLD® (a premix incorporating triclopyr by Zelam Ltd.).

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)), nonylphenol ethoxylate, benzylcocoalkyldimethyl quaternary ammonium salt, blend of petroleum hydrocarbon, alkyl esters, organic acid, and anionic surfactant, $C_9$-$C_{11}$ alkylpolyglycoside, phosphate alcohol ethoxylate, natural primary alcohol ($C_{12}$-$C_{16}$) ethoxylate, di-sec-butylphenol EO-PO block copolymer, polysiloxane-methyl cap, nonylphenol ethoxylate+urea ammonium nitrate, emulsified methylated seed oil, tridecyl alcohol (synthetic) ethoxylate (8 EO), tallow amine ethoxylate (15 EO), and PEG(400) dioleate-99.

In some embodiments, the additive is a safener that is an organic compound leading to better crop plant compatibility when applied with a herbicide. In some embodiments, the safener itself is herbicidally active. In some, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro[4.5]decane, oxabetrinil, 829148, and N-phenyl-sulfonylbenzoic acid amides, as well as agriculturally acceptable salts and, provided they have a carboxyl group, their agriculturally acceptable derivatives thereof. In some embodiments, the safener can be cloquintocet or an ester or salt thereof, such as cloquintocet (mexyl). For example, cloquintocet can be used to antagonize harmful effects of the compositions on rice and cereals.

Exemplary surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid or solid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like, esters of the above vegetable oils, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof. Exemplary solid carriers include, but are not limited to, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, pyrophyllite clay, attapulgus clay, kieselguhr, calcium carbonate, bentonite clay, Fuller's earth, cottonseed hulls, wheat flour, soybean flour, pumice, wood flour, walnut shell flour, lignin, ammonium sulfate, ammonium phosphate, ammonium nitrate, ureas, cereal meal, tree bark meal, wood meal and nutshell meal, cellulose powders, and mixtures thereof.

In some embodiments, emulsions, pastes, or oil dispersions can be prepared by homogenizing (a) and (b) in water by means of wetting agent, tackifier, dispersant or emulsifier. In some embodiments, concentrates suitable for dilution with water are prepared, comprising (a), (b), a wetting agent, a tackifier, and a dispersant or emulsifier.

In some embodiments, powders or materials for spreading and dusts can be prepared by mixing or concomitant grinding of (a) and (b) and optionally a safener with a solid carrier.

In some embodiments, granules (e.g. coated granules, impregnated granules and homogeneous granules) can be prepared by binding the (a) and (b) to solid carriers.

The formulations disclosed herein can comprise a synergistic, herbicidally effective amount of (a) and (b). In some embodiments, the concentrations of (a) and (b) in the formulations can be varied. In some embodiments, the formulations comprise from 1% to 95% (e.g., from 5% to 95%, from 10% to 80%, from 20% to 70%, from 30% to 50%) by total weight of (a) and (b). In some embodiments, (a) and (b), independently, can be employed in a purity of from 90% to 100% (e.g., from 95% to 100%) according to NMR spectrometry. In some embodiments, the concentrations of (a), (b), and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), and additional pesticides. In some embodiments, (a), (b), and additional pesticides, independently, can be employed in a purity of from 90% to 100% (e.g., from 95% to 100%) according to NMR spectrometry.

Methods of Application

The compositions disclosed herein can be applied in any known technique for applying herbicides. Exemplary application techniques include, but are not limited to, spraying, atomizing, dusting, spreading, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). In some embodiments, the compositions disclosed herein are applied post-emergence when the undesirable vegetation starts with leaf development up to flowering. In some embodiments, the compositions disclosed herein are applied post-emergence to relatively immature undesirable vegetation to achieve the maximum control of weeds. In some embodiments when the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applying to soil or water to prevent the emergence or growth of vegetation by spraying (e.g., foliar spraying). In some embodiments, the spraying techniques use, for example, water as carrier and spray liquor rates of from 10 liters per hectare (L/ha) to 2000 L/ha (e.g., from 50 L/ha to 1000 L/ha, or from 100 to 500 L/ha). In some embodiments, the compositions disclosed herein are applied by the low-volume or the ultra-low-volume method, wherein the application is in the form of micro-granules. In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

In some embodiments, wherein the undesirable vegetation is treated post-emergence, the compositions disclosed herein are applied by foliar application. In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the particle size of solid components, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The compositions and methods disclosed herein can be used to control undesired vegetation in a variety of crop and non-crop applications. In some embodiments, the compositions and methods disclosed herein can be used for controlling undesired vegetation in crops. Exemplary crops include, but are not limited to, sugar beets, mint, spinach, turnips, cereals such as wheat and wheat-like crops, rye, triticale and barley, corn or maize, oats, sorghum, rice, and sugar cane, pulse crops such as pea, bean and lentils, oilseed crops such as canola, oilseed rape and sunflower, fodder brassicas, forage crops such as alfalfa and clover, cotton, and soybean. In some embodiments, the compositions and methods disclosed herein can be used for controlling undesired vegetation in non-crop areas. Exemplary non-crop areas include, but are not limited to, turf, pasture, fallow, wildlife management areas, or rangeland. In some embodiments, the compositions and methods disclosed herein can be used in industrial vegetation management (IVM) or for utility, pipeline, roadside, and railroad rights-of-way applications. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program (CRP) lands, trees, vines, grasslands, and grasses grown for seeds. In some embodiments, the compositions and methods disclosed herein can be used on lawns (e.g., residential, industrial, and institutional), golf courses, parks, cemeteries, athletic fields, and sod farms.

The compositions and methods disclosed herein can also be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding. Exemplary resistant crops include, but are not limited to, corn or maize, sorghum, wheat, sunflower, rice, canola or oilseed rape, soybeans, cotton, alfalfa, clover, rye, barley, triticale, and sugar cane that are resistant to synthetic auxins, or crop plants that, owing to introduction of the gene for *Bacillus thuringiensis* (or Bt) toxin by genetic modification, are resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant crops possessing multiple or stacked traits conferring tolerance to multiple chemistries and/or multiple modes of action. In some embodiments, the undesired vegetation is controlled in phenoxy auxin tolerant crops and the phenoxy auxin tolerant crops have tolerance conferred by an AAD12 gene. The combination of (a), (b), and a complementary herbicide or salt or ester thereof can be used in combination with herbicides that are selective for the crop being treated and which complement the spectrum of weeds controlled by these compounds at the application rate employed.

The herbicidal compositions prepared and disclosed herein are effective against a variety of types of undesirable vegetation. In some embodiments, the compositions disclosed herein can be used for controlling broadleaf weeds. Exemplary broadleaf weeds include, but are not limited to, *Polygonum* species such as wild buckwheat (*Polygonum convolvulus*), *Amaranthus* species such as pigweed (*Amaranthus retroflexus*), *Chenopodium* species such as common lambsquarters (*Chenopodium album* L.), *Sida* species such as prickly sida (*Sida spinosa* L.), *Ambrosia* species such as common ragweed (*Ambrosia artemisiifolia*), *Acanthospermum* species, *Anthemis* species, *Atriplex* species, *Cirsium* species, *Convolvulus* species, *Conyza* species, such as horseweed (*Conyza canadensis*), *Cassia* species, *Commelina* species, *Datura* species, *Euphorbia* species, *Geranium* species, *Galinsoga* species, morning-glory (*Ipomoea* species), *Lamium* species, *Malva* species, *Matricaria* species, *Prosopis* species, *Rumex* species, *Sisymbrium* species, *Solanum* species, *Trifolium* species, *Xanthium* species, *Veronica* species, *Viola* species, common chickweed (*Stella ria media*), velvetleaf (*Abutilon theophrasti*), Hemp sesbania (*Sesbania exaltata* Cory), spurred anoda (*Anoda cristata*), common blackjack (*Bidens pilosa*), wild mustard (*Brassica kaber*), shepherd's purse (*Capsella bursa-pastoris*), cornflower (*Centaurea cyanus*), common hempnettle (*Galeopsis tetrahit*), cleavers (*Galium aparine*), common sunflower (*Helianthus annuus*), tall tick-clover (*Desmodium tortuosum*), Kochia (*Kochia scoparia*), spotted medick (*Medicago arabica*), annual mercury (*Mercurialis annua*), field forget-me-not (*Myosotis arvensis*), common poppy (*Papaver rhoeas*), jointed charlock (*Raphanus raphanistrum*), prickly saltwort (*Salsola kali*), wild mustard (*Sinapis arvensis*), field sowthistle (*Sonchus arvensis*), field pennycress (*Thlaspi arvense*), tall khakiweed (*Tagetes minuta*), Brazil callalily (*Richardia brasiliensis*), rat's-tail plantain (*Plantago major*), and narrow-leaved plantain (*Plantago lanceolata*). In some embodiments, the undesirable vegetation includes broomweed (*Sida acuta*).

By way of non-limiting illustration, examples of certain embodiments of the present disclosure are given below.

EXAMPLES

Evaluation of Aminocyclopyrachlor and Picloram for Post-Emergence Synergistic Weed Control Field trials were conducted with applications made to established grassland with naturally occurring weed populations. The target plants were treated with postemergence foliar applications when they were at the beginning of the flowering stage and 30 centimeters (11.8 inches) tall. All treatments were applied using a randomized complete block trial design, with four replications per treatment.

Treatments consisted of aminocyclopyrachlor in acid form and picloram-potassium, each in water and applied alone or in combination. Spray solutions were prepared using an appropriate amount of dilution to form a 2.0-liter (L) aqueous spray solution with active ingredients in single and two-way combinations. Formulated compounds were applied to the plant material with a backpack sprayer equipped with 8003 nozzles calibrated to deliver 400 liters per hectare (L/ha) at a spray height of 18-20 in (45-51 cm) above average plant canopy.

The treated plant was broomweed (Sida acuta, SIDAC). The treated plots and control plots were rated blind at various intervals after application. Ratings were based on a scale of 0-100%, as discussed above, wherein 0% indicates no damage to the undesired vegetation and 100% indicates complete destruction of the undesired vegetation Colby's equation was used to determine the herbicidal effects expected from the mixtures, as described above. The results were measured at 59 days, 75 days, and 88 days after the first application of the compositions. The trials exhibited unexpected synergy, and those results were found statistically significant under the p-value test. The herbicide tank mix combinations tested, application rates and ratios employed, plant species tested, and results are given below.

| Weed Bayer | Evaluation Interval | Aminocyclopyrachlor | | Picloram-Potassium | | Combination | |
|---|---|---|---|---|---|---|---|
| | | g ae/ha | Mean % weed control | g ae/ha | Mean % weed control | Measured mean % weed control | Colby predicted mean % weed control |
| SIDAC | 59 days | 150 | 42.5 | 180 | 6.3 | 72.5 | 46.1 |
| SIDAC | 75 days | 150 | 36.3 | 180 | 3.8 | 77.5 | 38.7 |
| SIDAC | 88 days | 150 | 41.3 | 180 | 5.5 | 81.3 | 44.5 |

As shown above, the samples demonstrated synergistic weed control, with higher measured weed control than would be predicted by the Colby equation.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A method of controlling undesirable vegetation, which comprises applying to vegetation or an area adjacent the vegetation or applying to soil or water to control the emergence or growth of vegetation a composition comprising a herbicidal active ingredient comprising (a) aminocyclopyrachlor, or an agriculturally acceptable salt or ester thereof and (b) picloram, or an agriculturally acceptable salt or ester thereof,
   wherein (a) and (b) are each added in an amount sufficient to provide a synergistic herbicidal effect,
   wherein the acid equivalent weight ratio of (a) to (b) is from 1:10 to 1.7:1,
   wherein the composition comprises at least one agriculturally acceptable adjuvant,
   wherein the undesirable vegetation comprises broomweed.

2. The method of claim 1, wherein (a) and (b) are applied postemergence to the undesirable vegetation.

3. The method of claim 1, wherein (a) includes aminocyclopyrachlor in acid form.

4. The method of claim 1, wherein (b) includes picloram potassium salt, picloram triisopropanolamine salt, picloram choline salt, or a mixture thereof.

5. The method of claim 1, wherein the undesirable vegetation is controlled in sugar beet, wheat, barley, corn or maize, sorghum, rice, cereals, CRP, oilseed rape or canola, trees and vines, grasses grown for seed, forestry, pastures, grasslands, rangelands, IVM, fallow land, sugar cane, rights-of-way, wildlife management areas, aquatics, or turf.

6. The method of claim 1, wherein the undesirable vegetation is controlled in crops tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof.

7. The method of claim 1, wherein the undesirable vegetation is controlled in phenoxy auxin tolerant crops and the phenoxy auxin tolerant crops have tolerance conferred by an AAD12 gene.

8. The method of claim 1, wherein (a) is applied in an amount of from 8-240 g ae/ha.

9. The method of claim 1, wherein (b) is applied in an amount of from 120-2400 g ae/ha.

10. The method of claim 1, wherein the herbicidal active ingredient consists of (a) aminocyclopyrachlor, or an agriculturally acceptable salt or ester thereof and (b) picloram, or an agriculturally acceptable salt or ester thereof.

11. The method of claim 1, wherein the acid equivalent weight ratio of (a) to (b) is from 1:5 to 5:3.

12. The method of claim 1, wherein the acid equivalent weight ratio of (a) to (b) is from 5:12 to 5:3.

* * * * *